(12) United States Patent
Koonankeil

(10) Patent No.: US 9,470,605 B2
(45) Date of Patent: Oct. 18, 2016

(54) METHOD OF INSPECTION FOR COOLING HOLES IN TURBINE AIRFOIL

(71) Applicant: UNITED TECHNOLOGIES CORPORATION, Hartford, CT (US)

(72) Inventor: James M. Koonankeil, Marlborough, CT (US)

(73) Assignee: United Technologies Corporation, Farmington, CT (US)

( * ) Notice: Subject to any disclaimer, the term of this patent is extended or adjusted under 35 U.S.C. 154(b) by 127 days.

(21) Appl. No.: 14/183,807

(22) Filed: Feb. 19, 2014

(65) Prior Publication Data

US 2015/0122998 A1 May 7, 2015

Related U.S. Application Data

(60) Provisional application No. 61/768,676, filed on Feb. 25, 2013.

(51) Int. Cl.
| | |
|---|---|
| *G01M 15/14* | (2006.01) |
| *G01N 25/72* | (2006.01) |
| *F01D 21/00* | (2006.01) |
| *G01M 99/00* | (2011.01) |
| *F01D 5/00* | (2006.01) |
| *F01D 5/18* | (2006.01) |
| *F01D 5/28* | (2006.01) |

(52) U.S. Cl.
CPC .............. *G01M 15/14* (2013.01); *F01D 5/005* (2013.01); *F01D 5/186* (2013.01); *F01D 5/288* (2013.01); *F01D 21/003* (2013.01); *G01M 99/002* (2013.01); *G01N 25/72* (2013.01); *F05D 2220/32* (2013.01); *F05D 2260/202* (2013.01); *F05D 2260/83* (2013.01)

(58) Field of Classification Search
CPC ...................................................... G01M 15/14
See application file for complete search history.

(56) References Cited

U.S. PATENT DOCUMENTS 6,564,935 B1 5/2003 Yamamoto et al.
2011/0235672 A1* 9/2011 Shepard et al. ................ 374/45

FOREIGN PATENT DOCUMENTS

WO    WO 2011131263 A1 * 10/2011

OTHER PUBLICATIONS

U.S. Appl. No. 61/892,541, filed Oct. 18, 2013.

* cited by examiner

*Primary Examiner* — Casey Bryant
*Assistant Examiner* — Jeremy S Valentiner
(74) *Attorney, Agent, or Firm* — Carlson, Gaskey & Olds, PC

(57) ABSTRACT

An airfoil has an of internal cooling channel, and cooling holes extending from the internal cooling channel to an outer skin. Air is injected into the cooling channel, and then into an inlet of the cooling hole. The exit of the air from an outlet of the cooling hole at the outer skin is monitored to determine whether the outlet is blocked. A location of the inlet of the cooling hole is determined by utilizing the determined location of the outlet, in combination with a known angle through which the cooling hole extends.

16 Claims, 3 Drawing Sheets

METHOD OF INSPECTION FOR COOLING HOLES IN TURBINE AIRFOIL

CROSS-REFERENCE TO RELATED APPLICATION

This application claims priority to U.S. Provisional Application No. 61/768,676, filed Feb. 25, 2013.

BACKGROUND OF THE INVENTION

This application relates to a method of inspecting the formation of cooling holes in a turbine airfoil.

Gas turbine engines are known and include a compressor compressing air and delivering it into a combustor where it is mixed with fuel and ignited. Products of this combustion pass downstream over turbine rotors, driving them to rotate. The turbine rotors, in turn, drive a compressor rotor.

The turbine rotors include a number of airfoils including rotating blades and static vanes. Turbine rotors, in particular, are subject to very high temperature from the products of combustion.

The turbine airfoils are typically provided with cooling channels and various cooling schemes for delivering cooling air. The airfoils are typically provided with cooling holes extending from internal cavities, which deliver cooling air to an outer skin of the airfoil. The outer skin of the airfoil is typically also provided with various coatings, as an example, a thermal barrier coating.

In quality control inspection of manufactured airfoils, many things must be checked. One thing checked is to ensure a deposited coating has not plugged any of the cooling holes. Also, even for uncoated airfoils, the inspection ensures the holes have been drilled through completely through to the internal cavities of the cooling channels, and have not been blocked by a drilling process. This may be done utilizing what is known as an infrared method. Air is injected into cooling channels within the airfoil and it leaves through the cooling holes at the outer skin. An infrared detector (such as an infrared camera) studies the location of the exit points and can tell if a particular cooling hole is plugged due to the infrared image captured from the surface.

Another quality control step that is performed is the hole true position inspection. Typically, a five axis vision based coordinate measurement machine is utilized. However, this machine typically measures the location of an outlet end of the cooling hole. A quality control system would find the location of the inlet end more important.

In addition, the prior art method requires that each hole be individually measured, which results in a long cycle time. Also, the use of the distinct machines for determining whether a cooling hole is plugged and for determining the true position of the hole requires that the inspection be performed on distinct platforms.

SUMMARY OF THE INVENTION

In a featured embodiment, a method of determining quality of manufacture of a component including the steps of forming a component having an internal cooling channel. Cooling holes extend from the internal cooling channel to an outer skin of the component. A coating is deposited on the outer skin. Air is injected into the internal cooling channel, and then into an inlet of the cooling hole, and then out of an outlet of the cooling hole. The exit is monitored of the air from the outlet at the outer skin to determine whether the outlet is clogged by the deposited coating. The location of the outlet is determined. A location of the inlet of the cooling hole is determined by utilizing the location of the outlet of the cooling hole, in combination with a known angle through which the cooling hole extends.

In another embodiment according to the previous embodiment, the monitoring of the exit of air is performed by an infrared detector.

In another embodiment according to any of the previous embodiments, a distance from the outer skin to the internal cooling channel is determined utilizing flash thermography.

In another embodiment according to any of the previous embodiments, the distance is also used to determine the location of the inlet of the cooling hole.

In another embodiment according to any of the previous embodiments, the component has an airfoil.

In another embodiment according to any of the previous embodiments, the infrared detector is an infrared camera.

In another embodiment according to any of the previous embodiments, the infrared camera is also a part of the flash thermography step.

In another embodiment according to any of the previous embodiments, the infrared camera captures images of the outer skin on a pixel by pixel basis.

In another embodiment according to any of the previous embodiments, a coating is deposited on the outer skin. The exit of air from the outlet at the outer skin is monitored to determine whether the outlet is clogged by a deposited coating.

In another embodiment according to nay of the previous embodiments, the exit of air from the outlet is monitored to determine whether the cooling hole has been fully drilled from the outlet to the inlet, and that it has not otherwise been clogged In another embodiment according to any of the previous embodiments, a distance from the outer skin to the internal cooling channel is determined utilizing flash thermography.

In another embodiment according to any of the previous embodiments, the infrared detector is an infrared camera and is also a part of the flash thermography step.

In another embodiment according to any of the previous embodiments, the infrared camera captures images of the outer skin on a pixel by pixel basis.

In another embodiment according to any of the previous embodiments, the distance is also used to determine the location of the inlet of the cooling hole.

In another embodiment according to any of the previous embodiments, the distance is also used to determine the location of the inlet of the cooling hole.

In another embodiment according to any of the previous embodiments, the component has an airfoil.

In another embodiment according to any of the previous embodiments, the component is a turbine blade.

In another embodiment according to any of the previous embodiments, the component has an airfoil.

In another embodiment according to any of the previous embodiments, the locations of the inlets of a plurality of the cooling holes are determined.

In another embodiment according to any of the previous embodiments, a distance from the outer skin to the internal cooling channel is also used to determine the location of the inlet of the cooling hole.

These and other features may be best understood from the following drawings and specification.

DETAILED DESCRIPTION

Figure 1A:
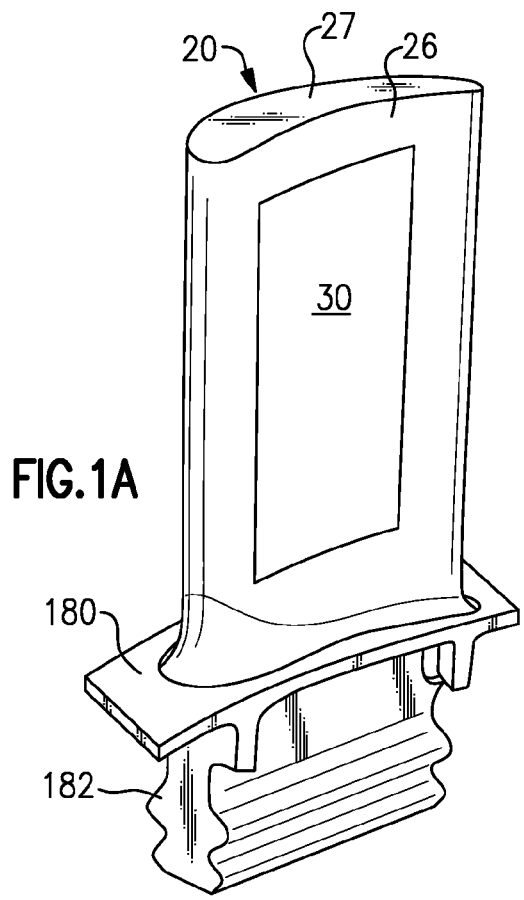
FIG. 1A shows a turbine airfoil.

FIG. 1A shows a turbine blade 20 having an airfoil 26 extending from a platform 180, and a dovetail 182 to secure the blade 20 within a turbine rotor. While a blade 20 is illustrated, the teachings of this application would extend to other turbine components having an airfoil, such as a vane. Internal cooling channel 30 is shown schematically in this figure, and extends radially from the platform 180 toward a radially outer tip 27.

Figure 1B:
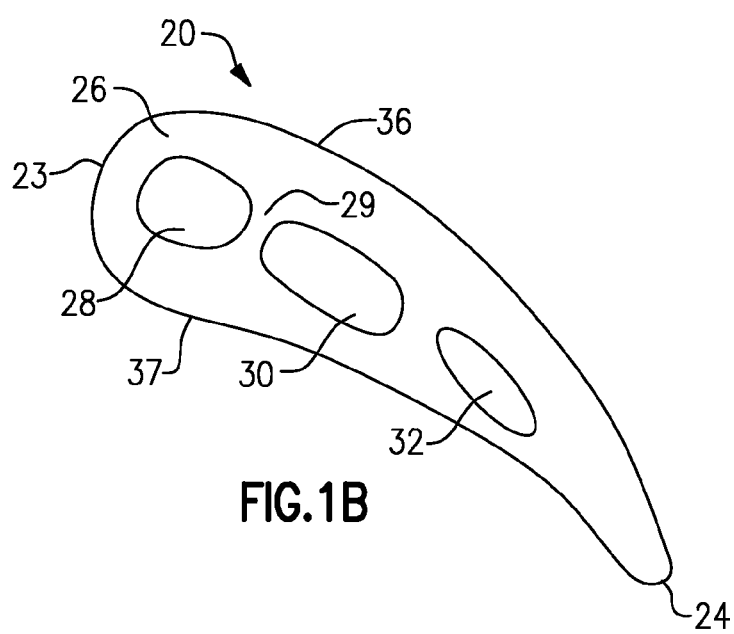
FIG. 1B is a cross-section.

As shown in FIG. 1B, a cross-section through the body of the airfoil 26 shows a suction side 36, a pressure side 37, a leading edge 23, and a trailing edge 24. A plurality of internal cooling channels 28, 30, and 32 extend along a radial dimension of the airfoil 26.

Figure 1C:
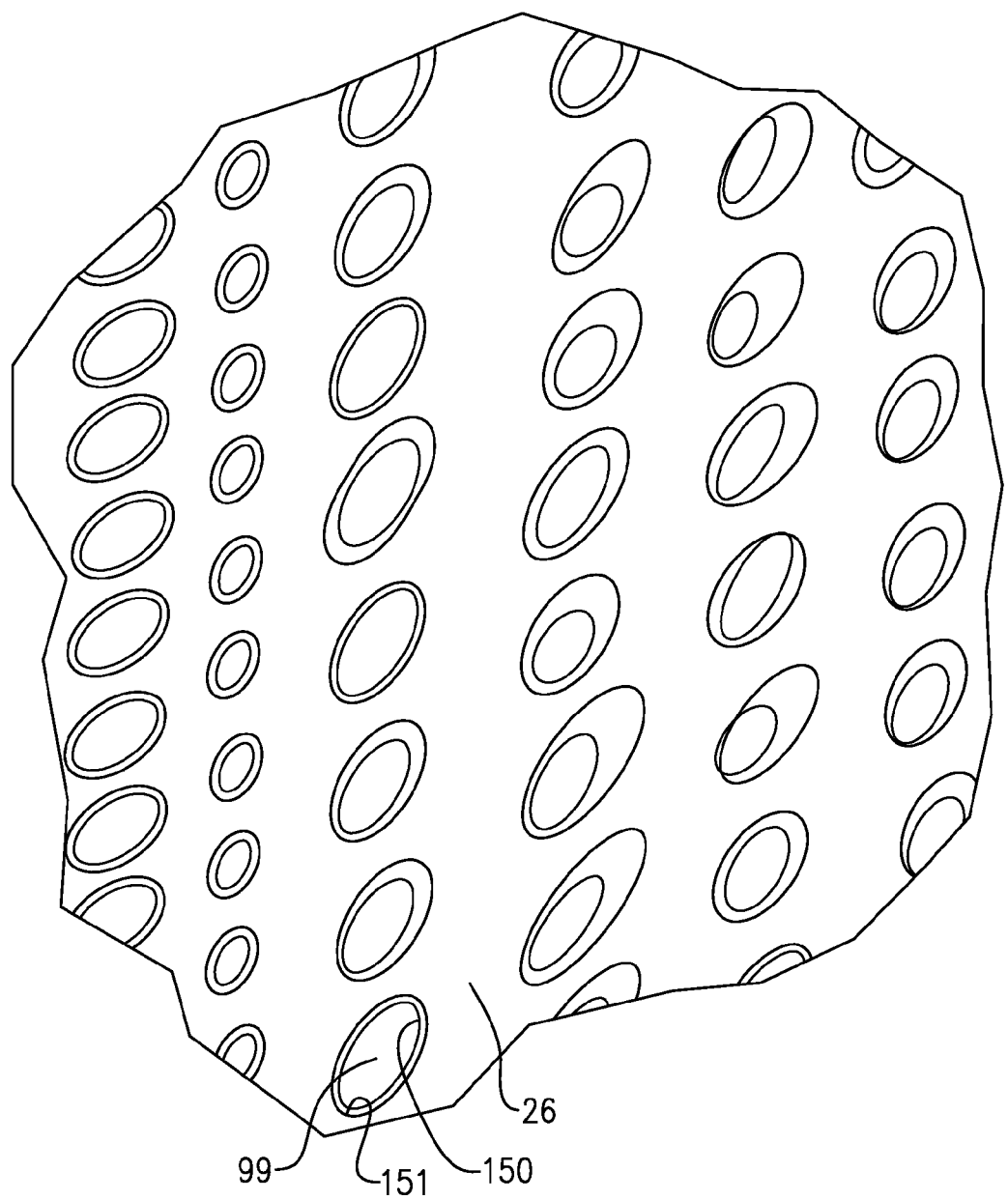
FIG. 1C shows a detail.

Cooling holes 99 are illustrated in FIG. 1C, and extend to the outer skin, at either the suction side 36, or pressure side 37. The cooling holes 99 as illustrated in FIG. 1C extend to an outlet 151 on the outer skin from an inlet 150 which communicates directly or indirectly with one of the internal cooling channels 28, 30 or 32.

As mentioned above, it is desirable to ensure that the location of the inlet 150 is as desired, and to further ensure that the outlet 151 is not clogged by a coating which is to be deposited on the airfoil 26.

Figure 2:
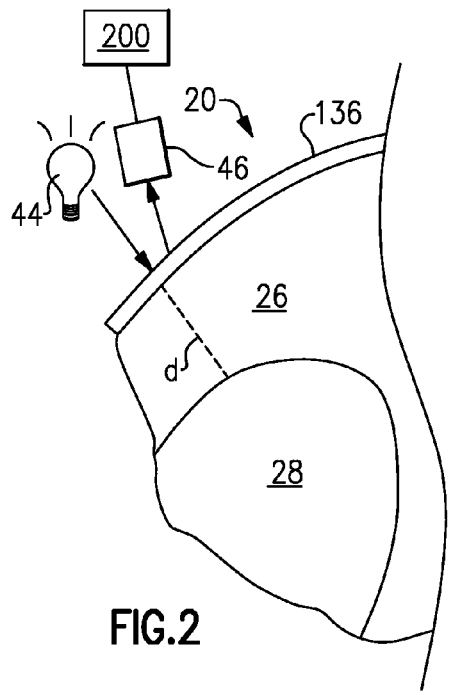
FIG. 2 shows a first method step.

FIG. 2 shows a first step. In FIG. 2, a flash thermography measurement is utilized to determine a distance d between an outer skin of the airfoil 26 and an internal cooling channel (here channel 28). The flash thermography system includes directing a flash of intense light from a source 44 against the outer skin. Then, an infrared detector (here camera 46) captures the reaction to the outer skin on a pixel by pixel basis over time and communicates that reaction to a computer control 200. The distance d can be determined by the rate of temperature change. As further shown in this view, a coating 36 is formed on the outer skin of the airfoil 26.

Figure 3:
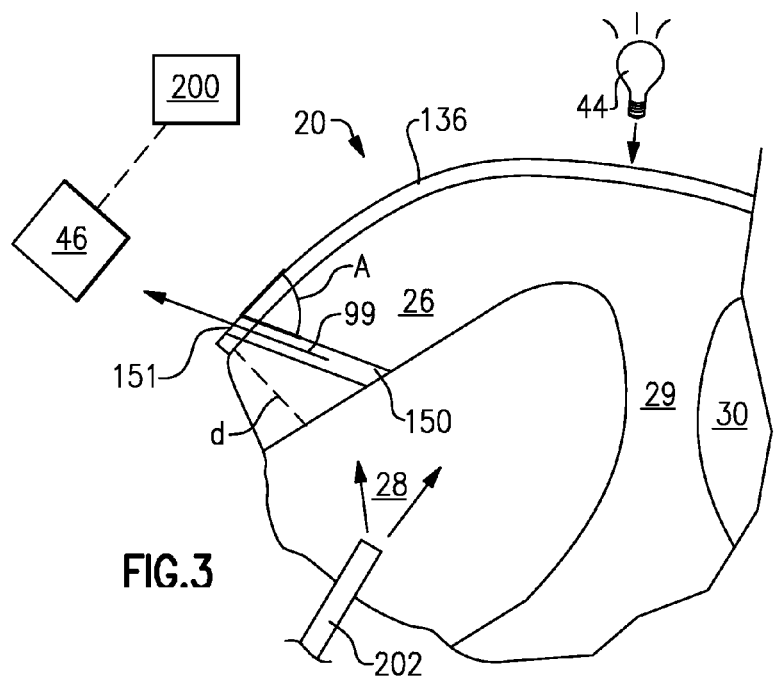
FIG. 3 shows a subsequent method step.

As shown in FIG. 3, the cooling hole 99 extends to an outlet 151, and from an inlet 150 communicating with an integrated cooling channel (here channel 28).

The infrared camera 46, communicating with the control 200, is shown in FIG. 3 performing two quality control checks. A source of air 202 injects air into the channel 28 and the air flows into the inlet 150, and out of the outlet 151 of the hole 99. The camera captures an image of this airflow, and can tell whether the particular hole 99 has been clogged by the deposited coating layer 136. This step can also occur on uncoated components, and can check to see whether the hole 99 has been completely drilled, or has been clogged in the drilling process.

In addition, the location of the outlet 151 is determined. An angle A of the hole 99 is known at the control 200 from the design of the blade 20. Thus, the true location of the inlet 150 can be determined by utilizing the angle A, the location of the outlet 151, and the distance d. As shown in FIG. 3, the flash thermography step utilizing source 44 can also determine the location of a rib 29 between the channels 28 and 30. Once this has occurred, the computer control 200 can also verify the inlet 150 is properly positioned relative to the rib 29.

Thus, this disclosure discloses a method that performs two important quality control steps in a single procedure that required two distinct locations and two distinct machine in the prior art. Moreover, the present disclosure provides information with regard to the location of inlet 150, which is an important aspect for quality control purposes.

Figure 4:
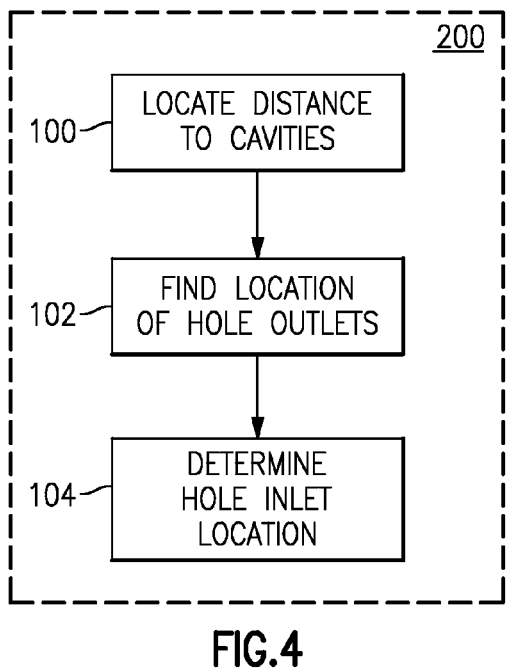
FIG. 4 is a flow chart.

FIG. 4 is a flow chart of what is occurring within control 200. First, a distance to the cavities is determined at step 100. Then, at step 102, the location of the hole outlets is determined. Finally, the true location of the hole inlet 150 is determined based upon the distance d, the location of the hole outlet 151, and stored information with regard to the angle A through which the hole 99 extends.

Although an embodiment has been disclosed, a worker of ordinary skill in this art would recognize that certain modifications would come within the scope of this invention. For that reason, the following claims should be studied to determine the true scope and content of this invention.

The invention claimed is:

1. A method of determining quality of manufacture of a component comprising the steps of:

forming a component having an internal cooling channel, and cooling holes extending from said internal cooling channel to an outer skin of said component;

injecting air into the internal cooling channel, and then into an inlet of said cooling hole, and then out of an outlet of said cooling hole and monitoring the exit of the air from the outlet at the outer skin to determine whether said outlet is at least slightly blocked and determining the location of the outlet; and determining a location of the inlet of said cooling hole by utilizing the location of said outlet of said cooling hole, in combination with a known angle through which the cooling hole extends, a distance from the outer skin to the internal cooling channel also being used to determine the location of the inlet of said cooling hole.

2. The method as set forth in claim 1, wherein said monitoring of the exit of air is performed by an infrared detector.

3. The method as set forth in claim 2, wherein said distance from the outer skin to the internal cooling channel is determined utilizing flash thermography.

4. The method as set forth in claim 3, wherein said component has an airfoil.

5. The method as set forth in claim 4, wherein said infrared detector is an infrared camera.

6. The method as set forth in claim 5, wherein said infrared camera is also a part of the flash thermography step.

7. The method as set forth in claim 6, wherein said infrared camera captures images of said outer skin on a pixel by pixel basis.

8. The method as set forth in claim 1, wherein a coating is deposited on said outer skin, and monitoring the exit of air from the outlet at the outer skin determines whether the outlet is clogged by a deposited coating.

9. The method as set forth in claim 1, wherein the monitoring of the exit of air from the outlet is utilized to determine whether the cooling hole has been fully drilled from the outlet to the inlet, and that it has not otherwise been clogged.

10. The method as set forth in claim 1, wherein said distance from the outer skin to the internal cooling channel is determined utilizing flash thermography.

11. The method as set forth in claim 10, wherein said infrared detector is an infrared camera and is also a part of the flash thermography step.

12. The method as set forth in claim 11, wherein said infrared camera captures images of said outer skin on a pixel by pixel basis.

13. The method as set forth in claim 10, wherein said component has an airfoil.

14. The method as set forth in claim 13, wherein said component is a turbine blade.

15. The method as set forth in claim 1, wherein said component has an airfoil.

16. The method as set forth in claim 1, wherein the locations of the inlets of a plurality of said cooling holes are determined.

* * * * *